(12) United States Patent  
Pschirer et al.

(10) Patent No.: US 8,609,846 B2
(45) Date of Patent: Dec. 17, 2013

(54) NAPHTHALENE MONOIMIDE DERIVATIVES AND USE THEREOF AS PHOTOSENSITIZERS IN SOLAR CELLS AND PHOTODETECTORS

(75) Inventors: Neil Gregory Pschirer, Mainz (DE); Jan Schoeneboom, Mannheim (DE); Felix Eickemeyer, Heidelberg (DE); Helmut Reichelt, Neustadt (DE); Ruediger Sens, Ludwigshafen (DE); Ingmar Bruder, Harthausen (DE)

(73) Assignee: BASF SE, Ludwigshafen (DE)

( * ) Notice: Subject to any disclaimer, the term of this patent is extended or adjusted under 35 U.S.C. 154(b) by 183 days.

(21) Appl. No.: 13/331,647

(22) Filed: Dec. 20, 2011

(65) Prior Publication Data

US 2012/0165530 A1    Jun. 28, 2012

Related U.S. Application Data

(60) Provisional application No. 61/425,822, filed on Dec. 22, 2010.

(51) Int. Cl.
   C07D 221/06   (2006.01)
   C07D 471/06   (2006.01)
   H01L 31/042   (2006.01)

(52) U.S. Cl.
   USPC .............................. 546/99; 546/52; 136/252

(58) Field of Classification Search
   USPC ...................... 546/99, 52; 136/252
   See application file for complete search history.

(56) References Cited

U.S. PATENT DOCUMENTS

| | | | |
|---|---|---|---|
| 4,927,721 | A | 5/1990 | Gratzel et al. |
| 5,350,644 | A | 9/1994 | Graetzel et al. |
| 6,359,211 | B1 | 3/2002 | Spitler et al. |
| 2012/0000533 | A1 | 1/2012 | Pschirer et al. |

FOREIGN PATENT DOCUMENTS

| | | |
|---|---|---|
| EP | 0 176 646 A1 | 4/1986 |
| JP | 10-189065 | 7/1998 |
| JP | 10-334954 | 12/1998 |
| JP | 2000-100484 | 4/2000 |
| JP | 2000-243463 | 9/2000 |
| JP | 2001-93589 | 4/2001 |
| WO | WO 01/00939 A1 | 1/2001 |
| WO | WO 01/45253 A2 | 6/2001 |
| WO | WO 2008/132103 A1 | 11/2008 |
| WO | WO 2010/136420 A1 | 12/2010 |

OTHER PUBLICATIONS

International Search Report Issued May 31, 2012 in Patent Application No. PCT/IB2011/055750.

Xiaomei Huang et al., "Novel dyes based on naphthalimide moiety as electron acceptor for efficient dye-sensitized solar cells", Dyes and Pigments, vol. 90, 2011, pp. 297-303.

U.S. Appl. No. 13/762,764, filed Feb. 8, 2013, Benedito et al.
U.S. Appl. No. 13/322,210, filed Nov. 23, 2011, Sundarraj et al.
U.S. Appl. No. 13/183,631, filed Jul. 15, 2011, Pschirer et al.

(Continued)

*Primary Examiner* — Charanjit Aulakh
(74) *Attorney, Agent, or Firm* — Oblon, Spivak, McClelland, Maier & Neustadt, L.L.P.

(57) ABSTRACT

The present invention relates to compounds of the formulae Ia and Ib

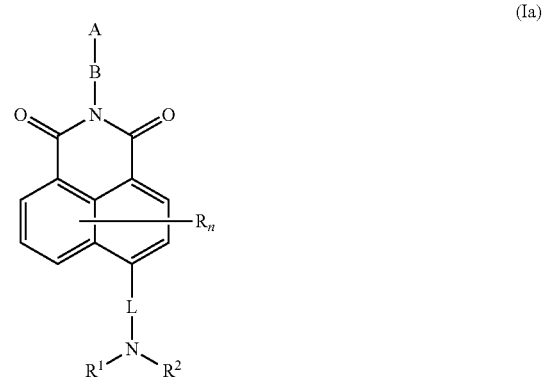

(Ia)

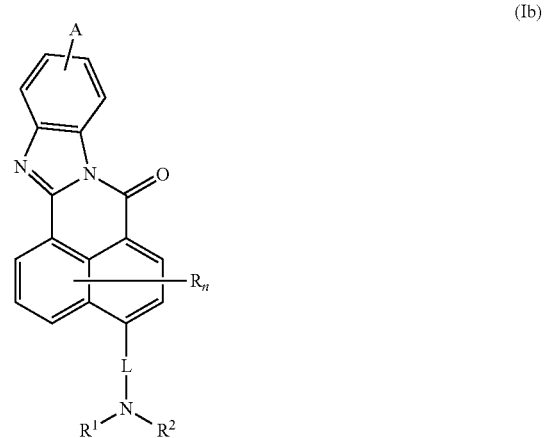

(Ib)

in which the variables R, n, A, B, $R^1$ and $R^2$ are each as defined in the description.

The present invention further relates to the use of compounds of the formula Ia or Ib or mixtures of compounds of the formulae Ia and Ib and/or isomers or mixtures of the isomers of the compounds of the formulae Ia and Ib as photosensitizers in solar cells and photodetectors, and to solar cells and photodetectors which comprise such compounds of the formula Ia or Ib or mixtures of compounds of the formulae Ia and Ib and/or isomers or mixtures of the isomers of the compounds of the formulae Ia and Ib as photosensitizers.

4 Claims, 2 Drawing Sheets

(56) References Cited

OTHER PUBLICATIONS

Brian O'Rogan, et al., "A low-cost, high-efficiency solar cell based on dye-sensitized colloidal $TiO_2$ films", Letters to Nature, vol. 353, Oct. 24, 1991, pp. 737-740.

U. Bach, et al., "Solid-state dye-sensitized mesoporous $TiO_2$ solar cells with high photon-to-electron conversion efficiencies", Letters to Nature, vol. 395, Oct. 8, 1998, pp. 583-585.

Suzanne Ferrere, et al., "New perylenes for dye sensitization of $TiO_2$", New J. Chem., 2002, vol. 26, pp. 1155-1160.

Sanghoon Kim, et al., "Molecular Engineering of Organic Sensitizers for Solar Cell Applications", J. Am. Chem. Soc., vol. 128, No. 51, 2006, pp. 16701-16707.

Hiromitsu Tanaka, et al., "Long-term durability and degradation mechanism of dye-sensitized solar cells sensitized with indoline dyes", Solar Energy Materials & Solar Cells 93, 2009, pp. 1143-1148.

Sanghoon Kim, et al., "The Role of Borole in a Fully Conjugated Electron-Rich System", ChemComm, 2004, 68-69.

NAPHTHALENE MONOIMIDE DERIVATIVES AND USE THEREOF AS PHOTOSENSITIZERS IN SOLAR CELLS AND PHOTODETECTORS

The present invention relates to compounds of the formulae Ia and Ib

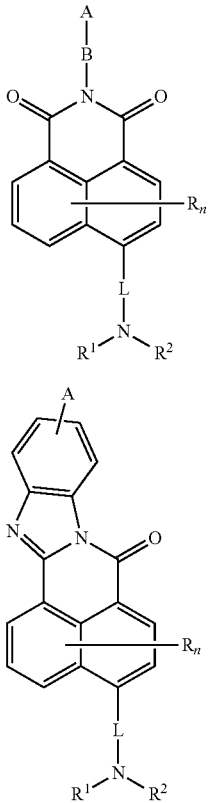

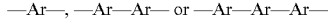

in which
R are identical or different aryloxy, arylthio, hetaryloxy or hetarylthio radicals,
n is 0, 1, 2, 3, 4 or 5,
B is $C_1$-$C_6$-alkylene or 1,4-phenylene, where the phenylene radical may be mono- or polysubstituted by alkyl, nitro, cyano and/or halogen,
A is —COOM, —$SO_3M$ or —$PO_3M$,
M is hydrogen, an alkali metal cation or $[NR']_4^+$,
R' is hydrogen or alkyl, where the R' radicals may be the same or different,
L is a bridge of the formula —Ar—, —Ar—Ar— or —Ar—Ar—Ar— which may be mono- or polysubstituted by phenyl, alkyl, alkoxy, alkylthio and/or —$NR^4R^5$, and in which Ar is aryl or hetaryl which may be fused to saturated or unsaturated 5- to 18-membered rings which may comprise heteroatoms which may be the same or different in the case of two or three Ar,
$R^4$, $R^5$ are each independently hydrogen, alkyl whose carbon chain may be interrupted by one or more —O—, —S—, —CO—, —SO— and/or —$SO_2$— moieties, aryl or hetaryl, each of which may be mono- or polysubstituted by alkyl, alkoxy and/or alkylthio,
$R^1$, $R^2$ are each independently radicals of the formula IIa or IIb

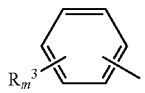

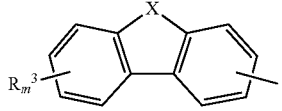

$R^3$ is phenyl, alkyl, alkoxy, alkylthio or —$NR^7R^8$,
m is 0, 1, 2, 3 or 4,
X is $C(R^6R^7)_2$, $NR^8$, oxygen or sulfur and
$R^6$, $R^7$, $R^8$ are each independently hydrogen, alkyl whose carbon chain may be interrupted by one or more —O—, —S—, —CO—, —SO— and/or —$SO_2$— moieties, aryl or hetaryl, each of which may be mono- or polysubstituted by alkyl, alkoxy and/or alkylthio.

The present invention further relates to the use of compounds of the formula Ia or Ib or mixtures of compounds of the formulae Ia and Ib and/or isomers or mixtures of the isomers of the compounds of the formulae Ia and Ib as photosensitizers in solar cells and photodetectors, and to solar cells and photodetectors which comprise such compounds of the formula Ia or Ib or mixtures of compounds of the formulae Ia and Ib and/or isomers or mixtures of the isomers of the compounds of the formulae Ia and Ib as photosensitizers.

The direct conversion of solar energy to electrical energy in solar cells is based on the internal photoeffect of a semiconductor material, i.e. the generation of electron-hole pairs by absorption of photons and the separation of the negative and positive charge carriers at a p-n junction or a Schottky contact. The photovoltage thus generated can bring about a photocurrent in an external circuit, through which the solar cell delivers its power.

The semiconductor can absorb only those photons which have an energy which is greater than its band gap. The size of the semiconductor band gap thus determines the fraction of sunlight which can be converted to electrical energy.

Thin layers or films of metal oxides are known to constitute inexpensive solid semiconductor materials (n-semiconductors), but their absorption, owing to large band gaps, is typically not within the visible region of the electromagnetic spectrum. For use in solar cells, the metal oxides therefore have to be combined with a photosensitizer which absorbs in the wavelength range of sunlight, i.e. at from 300 to 2000 nm, and, in the electronically excited state, injects electrons into the conduction band of the semiconductor. With the aid of a redox system which is used additionally in the cell and is reduced at the counterelectrode, electrons are recycled to the sensitizer which is thus regenerated.

Of particular interest for use in solar cells are the semiconductors zinc oxide, tin dioxide and especially titanium dioxide, which are used in the form of nanocrystalline porous layers. These layers have a large surface area which is coated with the sensitizer, so that high absorption of sunlight is achieved.

Dye-sensitized solar cells which are based on titanium dioxide as the semiconductor material are described, for example, in U.S. Pat. No. 4,927,721, Nature 353, p. 737-740 (1991) and U.S. Pat. No. 5,350,644, and also Nature 395, p. 583-585 (1998) and EP-A-1 176 646. These solar cells comprise monomolecular films of transition metal complexes, especially ruthenium complexes, which are bonded to the titanium dioxide layer via acid groups, as sensitizers and iodine/iodide redox systems present in dissolved form or amorphous organic p-conductors based on spirobifluorenes.

Also proposed repeatedly as sensitizers, not least for reasons of cost, have been metal-free organic dyes.

For example, U.S. Pat. No. 6,359,211 describes, for this purpose, cyanine, oxazine, thiazine and acridine dyes which have carboxyl groups bonded via an alkylene radical for securing to the titanium dioxide semiconductor.

Perylene-3,4:9,10-tetracarboxylic acid derivatives as sensitizers are examined in Japanese documents JP-A-10-189065, 2000-243463, 2001-093589, 2000-100484 and 10-334954, and in New J. Chem. 26, p. 1155-1160 (2002). The liquid electrolyte solar cells based on these perylene derivatives, however, exhibited much lower efficiencies than a solar cell sensitized with a ruthenium complex for comparison.

The most extensively examined sensitizers at present include dyes which possess a cyanoacrylate anchor group. For example, Kim, S.; Lee, J. K.; Kang, S. O.; Yum, j. H.; Fantacci, S.; DeAngelis, F.; Di Censo, D.; Nazeerruddin, M. K.; Grätzel, M. JACS 2006, 128, 16701 examines the compound

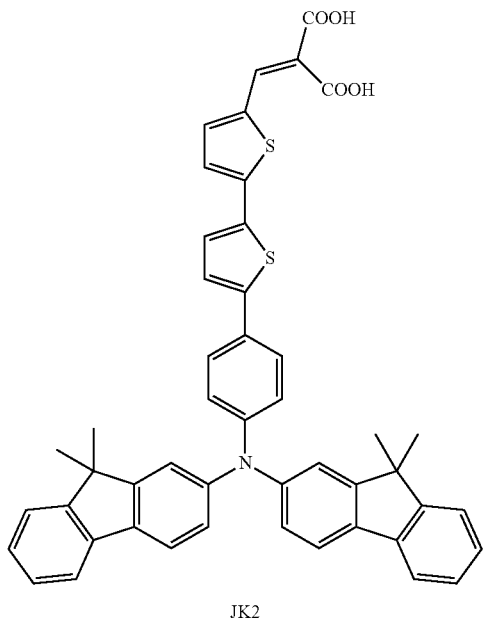 [SMILES: CC1(C)c2ccccc2-c2ccc(N(c3ccc(-c4ccc(-c5ccc(C=C(C(=O)O)C(=O)O)s5)s4)cc3)c3ccc4c(c3)C(C)(C)c3ccccc3-4)cc21]

JK2 and Solar Energy Materials & Solar Cells 2009, 93, 1143 examines the compound

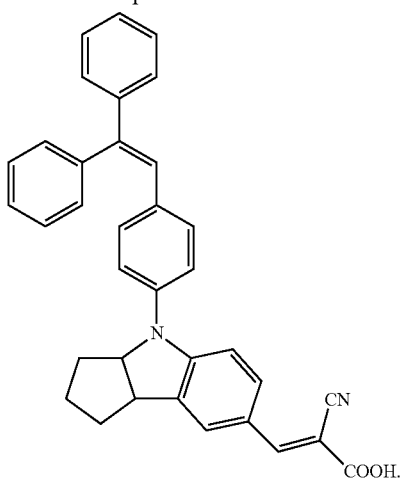

According to Solar Energy Materials & Solar Cells 2009, 93, 1143, however, the cyanoacrylate anchor groups are not sufficiently stable; decarboxylation of these dyes was found and it was suspected that the anchor groups are unstable to light.

Dyes with naphthalene monoimide anchor groups are described in the document WO 2008/132103 A1, but these compounds absorb in the short-wave spectral region of sunlight (absolute maximum at about 450 nm) and are therefore unsuitable for efficient absorption and conversion of sunlight.

It has now been found that, surprisingly, compounds of the formulae Ia and Ib of the present invention which comprise naphthalene monoimide groups as anchor groups exhibit good to very good quantum efficiencies with very good stabilities in dye solar cells.

Accordingly, the compounds of the formulae Ia and Ib detailed at the outset have been found, as has the use thereof as photosensitizers in solar cells and photodetectors.

In the context of the present invention, aryl is an aryl radical, unit or group, especially a radical with a base skeleton of 6 to 30 carbon atoms, preferably 6 to 18 carbon atoms, which is formed from one aromatic ring or a plurality of fused aromatic rings. Suitable base skeletons are, for example, phenyl, benzyl, naphthyl, anthracenyl or phenanthrenyl. This base skeleton may be unsubstituted, which means that all carbon atoms which are substitutable bear hydrogen atoms, or substituted at one, more than one or all substitutable positions of the base skeleton. Suitable substituents are, for example, alkyl radicals, preferably alkyl radicals having 1 to 8 carbon atoms, more preferably methyl, ethyl, i-propyl or t-butyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear a double bond, more preferably alkenyl radicals with one double bond and 1 to 8 carbon atoms, or groups with donor or acceptor action. Groups with donor action are understood to mean groups which have a +I and/or +M effect, and groups with acceptor action are understood to mean groups which have a −I and/or −M effect. Suitable groups with donor or acceptor action are halogen radicals, preferably F, Cl, Br, more preferably F, alkyl radicals, alkoxy radicals, aryloxy radicals, carbonyl radicals, ester radicals, amine radicals, amide radicals, $CH_2F$ groups, $CHF_2$ groups, $CF_3$ groups, CN groups, thio groups or SCN groups. The aryl radicals most preferably bear substituents selected from the group consisting of methyl, ethyl, iso-propyl, n-propyl, n-butyl, iso-butyl, tert-butyl, aryloxy, amine, thio groups and alkoxy, or the aryl radicals are unsubstituted. The aryl radical or the aryl group is preferably a phenyl radical which is optionally substituted by at least one of the aforementioned substituents. The phenyl radical more preferably has none, one, two or three of the aforementioned substituents.

In the context of the present invention, heteroaryl is a heteroaryl radical, unit or group, a radical which has 5 to 30, preferably 5 to 18, carbon atoms and/or heteroatoms and differs from the aforementioned aryl radicals in that at least one carbon atom in the base skeleton of the aryl radicals is replaced by a heteroatom. Preferred heteroatoms are N, O and S. Most preferably, one or two carbon atoms of the base skeleton of the aryl radicals are replaced by heteroatoms. The base skeleton is especially preferably selected from systems such as pyridyl, pyrimidyl, pyrazyl and triazolyl, and five-membered heteroaromatics such as pyrrole, furan, thiophene, imidazole, pyrazole, triazole, oxazole and thiazole. The base skeleton may be substituted at one, more than one or all substitutable positions of the base skeleton. Suitable substituents are the same as have already been mentioned for the aryl groups.

In the context of the present invention, the aryloxy, arylthio, hetaryloxy and hetarylthio radicals derive in a formal sense from the aforementioned aryl and heteroaryl radicals by attachment of an oxygen or sulfur atom to a carbon atom of the aryl or heteroaryl radical.

In the context of the present invention, alkyl is an alkyl radical, unit or group, especially a radical having 1 to 20 carbon atoms, preferably 1 to 12 carbon atoms. This alkyl radical may be branched or unbranched and optionally be interrupted by one or more —O—, —S—, —CO—, —SO— and/or —SO$_2$— moieties. Alkyl is more preferably selected from the group consisting of methyl, ethyl, i-propyl, n-propyl, i-butyl, n-butyl, t-butyl, sec-butyl, i-pentyl, n-pentyl, sec-pentyl, neopentyl, n-hexyl, i-hexyl and sec-hexyl.

In the context of the present invention, alkoxy and alkylthio radicals derive in a formal sense from the aforementioned alkyl radicals by attachment of an oxygen or sulfur atom to a carbon atom of the alkyl radical.

In the context of the present invention, halogen is preferably F, Cl or Br, more preferably F.

In the context of the present invention, alkali metal cation is preferably Li, Na, Cs or K, more preferably Na.

When the bridge L is mono- or polysubstituted by phenyl, alkyl, alkoxy, alkylthio and/or —NR$^4$R$^5$, this means that these substituents are attached to suitable positions on the aromatic and heteroaromatic Ar groups.

When the bridge L comprises two or three Ar, they may be the same or different.

Examples of suitable Ar include 1,4-, 1,3- and 1,2-phenylene, 1,4- and 1,8-naphthylene, 1,4- and 2,3-pyrrylene, 2,5-, 2,4- and 2,3-thienylene, 2,5-, 2,4- and 2,3-furanylene, 2,3-, 2,4-, 2,5-, 2,6-, 3,4- and 3,5-pyridinylene, 2,3-, 2,5-, 2,6-, 3,7-, 4,8-, 5,8- and 6,7-quinolinylene, 2,7-, 3,6-, 4,5-, 2,6-, 3,7-, 4,7- and 4,8-isoquinolinylene, 1,4-[2,5-di(tert-butyl)]phenylene, 1,4-(2,5-dihexyl)phenylene, 1,4-[2,5-di(tert-octyl)]phenylene, 1,4-(2,5-didodecyl)phenylene and 1,4-[2,5-di(2-dodecyl)]phenylene. Especially useful as Ar are 1,4-phenylene and 2,5-thienylene.

Suitable bridges L are, for example:

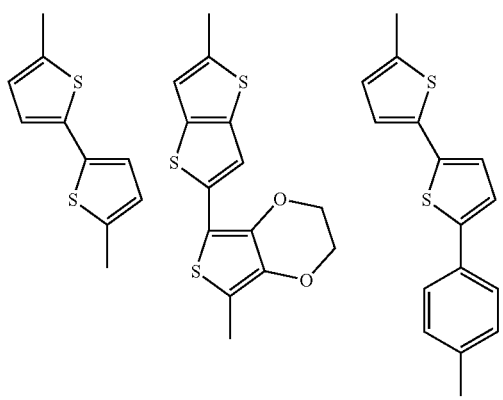

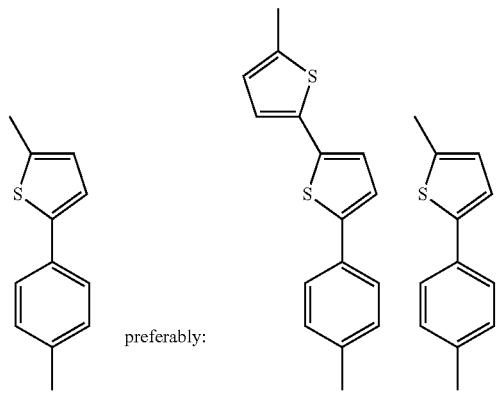

preferably:

Preference is given to inventive compounds in which, in the formulae Ia and Ib:
R are identical or different aryloxy or arylthio, especially phenoxy or phenylthio, radicals,
n is 0, 1 or 2,
B is C$_1$-C$_6$-alkylene, especially —CH$_2$—, —(CH$_2$)$_2$— and —(CH$_2$)$_3$—,
A is —COOM,
M is hydrogen or an alkali metal cation,
L is a bridge of the formula —Ar—Ar— or —Ar—Ar—Ar— which may be mono- or polysubstituted by phenyl, C$_1$-C$_{12}$-alkyl, C$_1$-C$_{12}$-alkoxy, C$_1$-C$_{12}$-alkylthio and/or —NR$^4$R$^5$, and in which Ar is identical or different aryl or hetaryl which may be fused to saturated or unsaturated 5- to 18-membered rings which may comprise heteroatoms,
R$^4$, R$^5$ are each independently hydrogen, C$_1$-C$_{12}$-alkyl whose carbon chain may be interrupted by one or more —O—, —S—, —CO—, —SO— and/or —SO$_2$— moieties,
R$^1$, R$^2$ are each independently radicals of the formulae II'a and II'b

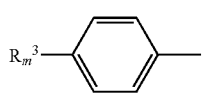
(II'a)

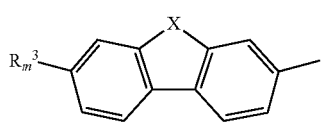
(II'b)

R$^3$ is C$_1$-C$_{12}$-alkoxy,
m is 0 or 1,
X is C(R$^6$R$^7$)$_2$, NR$^8$, oxygen or sulfur and
R$^6$, R$^7$, R$^8$ are each independently hydrogen, C$_1$-C$_{12}$-alkyl whose carbon chain may be interrupted by one or more —O—, —S—, —CO—, —SO— and/or —SO$_2$— moieties.

Particular preference is given to inventive compounds in which, in the formulae Ia and Ib,
n is 0,
B is C$_1$-C$_6$-alkylene, especially —CH$_2$— and —(CH$_2$)$_2$—,
A is —COOM,
M is hydrogen or an alkali metal cation, L is a bridge of the formula —Ar—Ar— or —Ar—Ar—Ar— in which Ar is identical or different aryl or hetaryl, $R^1$, $R^2$ are each independently radicals of the formulae II'a and II'b

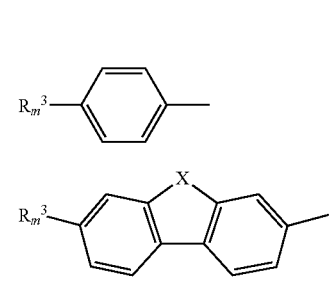

(II'a)

(II'b)

$R^3$ is $C_1$-$C_{12}$-alkoxy, m is 0 or 1,

X is $C(R^6R^7)_2$ and $R^6$, $R^7$ are each independently hydrogen or $C_1$-$C_{12}$-alkyl.

The invention shall encompass not only the compounds of the formulae Ia and Ib and the preferred embodiments thereof, but also mixtures thereof, the isomers thereof and the mixtures of the isomers.

For example, the invention also includes isomeric compounds of the formula I*b shown below:

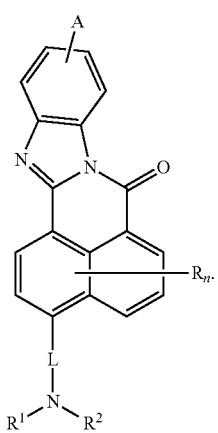

(I*b)

EXAMPLES

Example 1

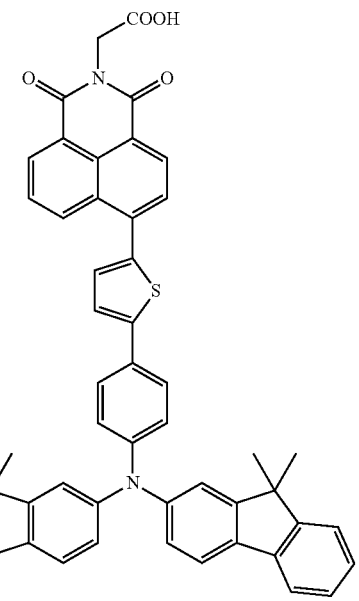

Ia

The preparation (according to Ko et al. Chemical Communications, 2004, 68-69) proceeded from (4-bromophenyl)bis(9,9-dimethyl-9H-fluoren-2-yl)amine, which was first reacted with thiophene-2,5-diboronic ester

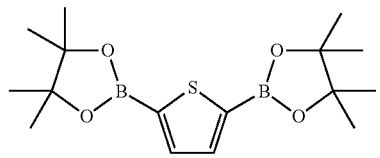

(step a). This was followed by the coupling with the methyl ester of N-(2-carboxyethyl)-4-chloronaphthalimide and deprotection of the ester group (step b).

Step a):

A mixture of 1.66 g (2.98 mmol) of (4-bromophenyl)bis(9,9-dimethyl-9H-fluoren-2-yl)amine, 2.00 g (5.96 mmol) of thiophene-2,5-diboronic ester, 0.82 g (5.96 mmol) of $K_2CO_3$ dissolved in 5.2 mL of 10:1 $H_2O$/ethanol, 92 mg (0.06 mmol) of $Pd(PPh_3)_4$ and 10 mL of toluene was heated to 85° C. under nitrogen and stirred at this temperature for 4 h.

After cooling, the reaction mixture was filtered off with suction. The mother liquor was extracted by shaking with dichloromethane/$H_2O$. The solvent was removed from the organic phase and the residue was dried. The crude product was used unpurified in the next reaction step.

Step b):

A mixture of 2.00 g of stage a crude product, 1.33 g (4.38 mmol) of the methyl ester of N-(2-carboxyethyl)-4-chloronaphthalimide, 50.4 mg (0.055 mmol) of $Pd_2(dba)_3$, 1.43 g (4.38 mmol) of $Cs_2CO_3$, 26.3 mg (0.13 mmol) of tributylphosphine and dioxane was heated to 90° C. and stirred at this temperature for 6 h. After cooling, the reaction mixture was filtered off with suction and then the solvent was removed from the mother liquor. The crude product was purified by column chromatography with n-hexane/ethyl acetate (2:1). 70 mg of the protected compound were obtained.

The latter was stirred with 200 mg of KOH in 10 mL of 1:1 demineralized water:THF at 60° C. for one day. After cooling, 10 mL of conc. HCl were added and the mixture was stirred for 1 h. Then the reaction mixture was added to demineralized water. The solid was filtered off with suction, washed with hot demineralized water and dried.

The purification was effected by column chromatography with the eluent 10:1 dichloromethane:ethanol+2% trimethylamine. The solid obtained was extracted by stirring with 50% acetic acid at 60° C., filtered off with suction and washed with hot demineralized water. After drying, 1.2 g of a red solid were obtained.

Analytical Data $^1$H NMR (500 MHz, CDCl3, 25° C.): δ=8.79 (d, 1H); 8.68 (d, 1H); 8.63 (d, 1H); 7.88 (d, 1H); 7.80 (q, 1H), 7.66 (d, 2H); 7.63 (d, 2H); 7.58 (d, 2H); 7.40 (t, 3H); 7.33 (m, 3H); 7.27 (m, 4H); 7.23 (d, 2H); 7.15 (d, 2H); 5.02 (s, 2H); 1.43 (s, 12H)

Example 2

2a

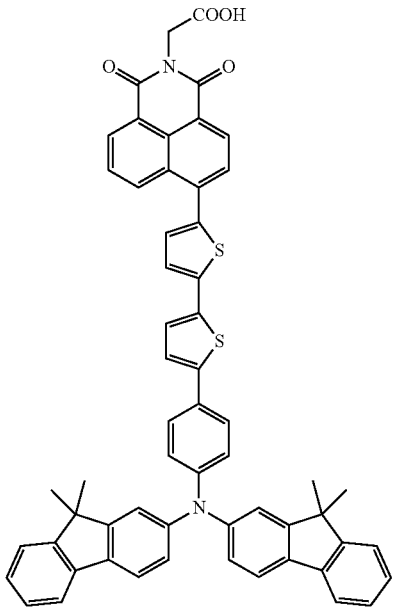

The preparation (according to Ko et al., Chemical Communications, 2004, 68-69) proceeded from (4-bromophenyl)bis(9,9-dimethyl-9H-fluoren-2-yl)amine, which was first reacted with 2,2-bisthiophene-5-boronic ester (step a). This was followed by the bromination (step b) and then the coupling with the 4-boronic ester naphthalimide of the structure

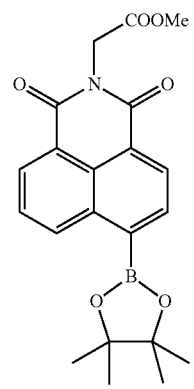 [SMILES: COC(=O)CN1C(=O)c2cccc3c(B4OC(C)(C)C(C)(C)O4)ccc(c23)C1=O]

and deprotection of the ester group (step c).

Step a:

A mixture of 1.67 g (3.00 mmol) of (4-bromophenyl)bis(9,9-dimethyl-9H-fluoren-2-yl)amine, 1.80 mL (9.00 mmol) of 5 molar NaOH and 10 mL of dioxane was degassed with argon for 30 min. Then 54 mg (0.160 mmol) of Pd[P(tBu)$_3$]$_2$ and 1.00 g (3.42 mmol) of 2,2-bisthiophene-5-boronic ester

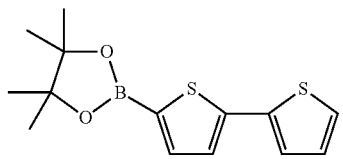 [SMILES: CC1(C)OB(c2ccc(-c3cccs3)s2)OC1(C)C]

were added, and the mixture was heated to 85° C. and stirred over the weekend. After cooling, the reaction mixture was added to ice-water. Subsequently, it was extracted with dichloromethane and the solvent was removed from the organic phase. The residue was dissolved in a little tetrahydrofuran. Methanol was added thereto until a solid precipitated out. The latter was filtered off with suction, washed with a little methanol and dried. 1.40 g of a yellow solid were obtained, which corresponds to a yield of 73%.

Analytical Data:

$^1$H NMR (500 MHz, DMSO, 25° C.): δ=7.77 (m, 4H); 7.62 (d, 2H); 7.51 (d, 3H); 7.41 (d, 1H); 7.31 (m, 8H); 7.11 (m, 3H); 7.05 (d, 2H); 1.37 (s, 12H)

Step b:

A solution of 466 mg (2.62 mmol) of N-bromosuccimide and 10 mL of DMF was added dropwise at 0-5° C. to a mixture of 1.40 g (2.18 mmol) of stage a and 20 mL of dimethylformamide (DMF). Stirring was then continued at this temperature for 15 min and then 10 mL of dilute sodium thiosulfate solution were added. The reaction mixture was added to 150 mL of demineralized water and extracted with methyl tert-butyl ether (MTBE). The solvent was removed from the organic phase and the residue was dried. 1.20 g of a yellow solid were obtained, which corresponds to a yield of 76%.

Analytical Data:

$^1$H NMR (500 MHz, DMSO, 25° C.): δ=7.77 (m, 4H); 7.62 (d, 2H); 7.51 (d, 2H); 7.42 (d, 1H); 7.31 (m; 7H); 7.23 (d, 1H); 7.17 (d, 1H); 7.11 (d, 2H); 7.06 (d, 1H); 1.37 (s, 12H)

Step c:

A mixture of 1.00 g (1.4 mmol) of stage b, 0.84 mL (4.2 mmol) of 5 molar NaOH and 15 mL of dioxane was degassed with argon for 30 min. Then 24 mg (0.05 mmol) of Pd[P(tBu)$_3$]$_2$ and 0.97 g (1.6 mmol) of the 4-boronic ester naphthalimide (65%) shown above were added, and the mixture was heated to 85° C. and stirred for 1 day. After cooling, the reaction mixture was added to ice-water and extracted with dichloromethane. The solvent was removed from the organic phase. The residue was purified by means of column chromatography with the eluent 4:1 dichloromethane:methanol.

Protected target product was obtained, which was stirred with 1:1 THF:water and 1 g of KOH at 65° C. overnight. After cooling, the reaction mixture was added to water, and 15 mL of conc. HCl were added. The mixture was stirred at room temperature for 1 h. Then the solid was filtered off with suction, washed and dried. The crude product was purified by means of column chromatography with the eluent 4:1 dichloromethane:methanol. This gave 330 mg of a red solid, which corresponds to a yield of 26%.

Analytical Data:
$^1$H NMR (500 MHz, DMSO, 25° C.): δ=8.80 (d, 1H); 8.61 (d, 1H); 8.55 (d, 1H); 7.99 (q, 2H); 7.76 (g, 4H); 7.65 (d, 2H); 7.55 (q, 2H); 7.51 (d, 2H); 7.47 (d, 2H); 7.30 (m, 6H); 7.12 (d, 2H); 7.06 (d, 2H); 4.75 (s, 2H); 1.34 (s, 12H)

Example 3

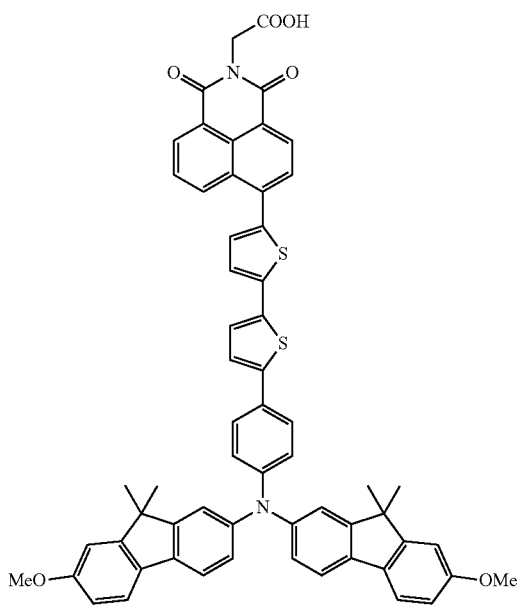

3a

The preparation proceeded from diarylamine, which was first reacted with bisthiophene-5-boronic ester (step a). This was followed by bromination (step b) and then coupling with 2-boronic ester naphthalimide (step c):

Step a:

A mixture of 1.80 g (2.9 mmol) of diarylamine, 15 mL of dioxane and 1.74 mL (8.7 mmol) of 5 molar NaOH was degassed with argon for 30 min. Then 51 mg (0.1 mmol) of Pd[P(tBu)$_3$]$_2$ and 0.91 g (3.11 mmol) of bisthiophene-5-boronic ester were added, and the mixture was heated to 85° C. and stirred over the weekend. After cooling, the reaction mixture was added to ice-water and extracted with dichloromethane. The solvent was removed from the organic phase, and the residue was dissolved in a little THF and methanol was added. The precipitated solid was filtered off with suction and dried. The purification was effected by means of column chromatography with the eluent n-hexane+2% ethyl acetate. This gave 1.70 g of a yellow solid, which corresponds to a yield of 85%.

Analytical Data:
$^1$H NMR (500 MHz, DMSO, 25° C.): δ=7.41 (d, 4H); 7.34 (d, 2H); 7.26 (d, 1H); 7.14 (d, 1H); 7.08 (d, 1H); 7.04 (d, 1H); 6.99 (d, 2H); 6.86 (d, 3H); 6.81 (d, 2H); 6.76 (d, 2H); 6.65 (d, 2H); 3.56 (s, 6H); 1.11 (s, 12H)

Step b:

A solution of 490 mg (2.40 mmol) of N-bromosuccimide and 10 mL of DMF was added dropwise at 0-5° C. to a mixture of 1.6 g (2.3 mmol) of stage a and 30 mL of DMF. Stirring was then continued at this temperature for 15 min and then 10 mL of dilute sodium thiosulfate solution were added. The reaction mixture was added to 150 mL of demineralized water. The solid was filtered off with suction, washed and dried. 1.62 g of a yellow solid were obtained, which corresponds to a yield of 90%.

Analytical Data:
$^1$H NMR (500 MHz, DMSO, 25° C.): δ=7.66 (d, 4H); 7.58 (d, 2H); 7.40 (d, 1H); 7.30 (d, 1H); 7.26 (d, 2H); 7.23 (d, 1H); 7.16 (d, 1H); 7.11 (d, 2H); 7.07 (d, 2H); 7.01 (d, 2H); 6.90 (d, 2H); 3.81 (s, 6H); 1.36 (s, 12H)

Step c:

A mixture of 1.00 g (1.3 mmol) of stage b, 0.78 mL (3.9 mmol) of 5 molar NaOH and 15 mL of dioxane was degassed with argon for 30 min. Then 26 mg (0.05 mmol) of Pd[P(tBu)$_3$]$_2$ and 0.59 g (1.5 mmol) of the compound

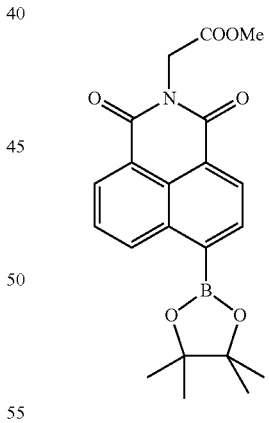

were added, and the mixture was heated to 85° C. and stirred for 1 day. After cooling, the reaction mixture was added to ice-water and extracted with dichloromethane. The solvent was removed from the organic phase. The residue was purified twice by means of column chromatography with the eluent 4:1 dichloromethane:methanol. This gave 630 mg of a red solid, which corresponds to a yield of 68%.

Analytical Data:
$^1$H NMR (500 MHz, DMSO, 25° C.): δ=8.75 (d, 1H); 8.58 (d, 1H); 8.51 (d, 1H); 7.96 (m, 2H); 7.65 (d, 4H); 7.62 (d, 2H);

7.53 (s, 2H); 7.45 (s, 2H); 7.26 (d, 2H); 7.11 (d, 2H); 7.07 (d, 2H); 7.02 (d, 2H); 6.90 (d, 2H); 4.51 (s, 2H); 3.81 (s, 6H); 1.36 (s, 12H)

Example 4

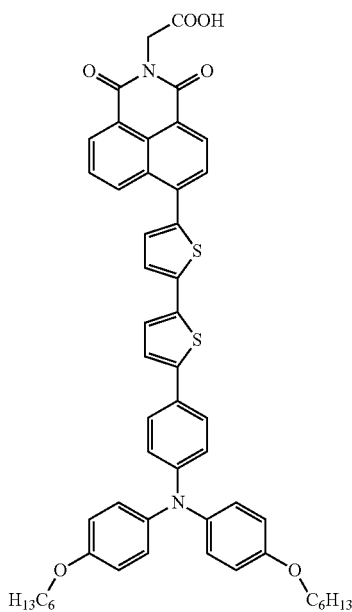

4a

The preparation proceeds from 4-hexyloxybromobenzene, which was reacted with p-hexyloxybromobenzene (step a). The resulting amine was reacted further with 1,4-dibromobenzene (step b). This was followed by coupling with 2,2-bisthiophene-5-boronic ester (step c) and bromination (step d). Finally, coupling was effected with 2-boronic ester naphthalimide and the ester group was deprotected (step e).

Step a:

A mixture of 20 g (78 mmol) of 4-hexyloxybromobenzene, 18 g (93 mmol) of p-hexyloxybromobenzene, 0.87 g (3.9 mmol) of palladium(II) acetate, 3.1 g (5.8 mmol) of DPEphos, 12 g (125 mmol) of sodium tert-butoxide and 100 mL of toluene was heated to 100° C. and stirred for one day. After cooling, the solvent was removed from the reaction mixture. The crude product was purified by means of column chromatography with the eluent 2:1 dichloromethane:hexane. 19.7 g of a white solid were obtained, which corresponds to a yield of 68%.

Analytical Data:
$^1$H NMR (500 MHz, CD2Cl2, 25° C.): δ=6.91 (d, 4H); 6.79 (d, 4H); 5.35 (s, 1H); 3.90 (t, 4H); 1.74 (m, 4H); 1.45 (m, 4H); 1.34 (m, 8H); 0.91 (t, 6H);

Step b:

A mixture of 5.4 g (14.6 mmol) of stage a, 6.9 g (29.2 mmol) of 1,4-dibromobenzene, 275 mg (0.30 mmol) of Pd$_2$(dba)$_3$, 405 mg (0.73 mmol) of DPPF, 2.80 g (29.2 mmol) of sodium tert-butoxide and 40 mL of toluene was heated to 90° C. and stirred for 2 days. After cooling, the solvent was removed from the reaction mixture. The purification was effected by means of column chromatography with the eluent 4:1 hexane:dichloromethane. 5.6 g of a light-colored oil were obtained, which corresponds to a yield of 72%.

Analytical Data:
$^1$H NMR (500 MHz, DMSO, 25° C.): δ=7.29 (d, 2H); 6.99 (d, 4H); 6.89 (d, 4H); 6.66 (d, 2H); 3.92 (t, 4H); 1.69 (m, 4H); 1.40 (m, 4H); 1.30 (m, 8H); 0.88 (t, 6H)

Step c:

A mixture of 1.6 g of stage b (3.1 mmol), 15 mL of dioxane and 1.86 mL (9.3 mmol) of 5 molar NaOH was degassed with argon for 30 min. Then 51 mg (0.11 mmol) of Pd[P(tBu)$_3$]$_2$ and 0.98 g (3.31 mmol) of 2,2-bisthiophene-5-boronic ester were added, and the mixture was heated to 85° C. and stirred over the weekend. After cooling, the reaction mixture was added to ice-water and extracted with dichloromethane. The solvent was removed from the organic phase. The purification was effected by means of column chromatography with the eluent n-hexane+2% ethyl acetate. This gave 1.62 g of a yellow solid, which corresponds to a yield of 86%.

Analytical Data:
$^1$H NMR (500 MHz, DMSO, 25° C.): δ=7.48 (m, 3H); 7.30 (m, 2H); 7.25 (d, 1H); 7.09 (q, 1H); 7.03 (q, 4H); 6.92 (q, 4H); 6.76 (q, 2H); 3.94 (t, 4H); 1.70 (m, 4H); 1.41 (m, 4H); 1.31 (m, 8H); 0.88 (t, 6H)

Step d:

A solution of 430 mg (2.40 mmol) of N-bromosuccimide and 10 mL of DMF was added dropwise at 0-5° C. to a mixture of 1.2 g (2.00 mmol) of stage c and 30 mL of DMF. Stirring was then continued at this temperature for 15 min and then 10 mL of dilute sodium thiosulfate solution were added. The reaction mixture was added to 150 mL of demineralized water and extracted with MTBE, and the solvent was removed from the organic phase. 1.0 g of a yellow solid was obtained, which corresponds to a yield of 73%.

Analytical Data:
$^1$H NMR (500 MHz, DMSO, 25° C.): δ=7.46 (d, 2H); 7.29 (d, 1H); 7.27 (d, 1H); 7.21 (d, 1H); 7.14 (d, 1H); 7.03 (d, 4H); 6.92 (d, 4H); 6.75 (d, 2H); 3.94 (t, 4H); 1.70 (m, 4H); 1.41 (m, 4H); 1.31 (m, 8H); 0.98 (t, 6H)

Step e:

A mixture of 0.90 g (1.3 mmol) of stage d, 0.78 mL (3.9 mmol) of 5 molar NaOH and 15 mL of dioxane was degassed with argon for 30 min. Then 22 mg (0.04 mmol) of Pd[P(tBu)$_3$]$_2$ and 0.91 g (1.5 mmol) of the compound

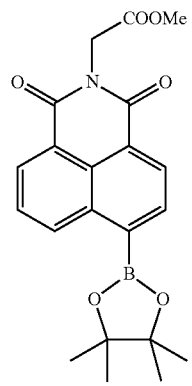 [SMILES: COC(=O)CN1C(=O)c2cccc3c(B4OC(C)(C)C(C)(C)O4)ccc(c23)C1=O]

were added, and the mixture was heated to 85° C. and stirred for 1 day. After cooling, the reaction mixture was added to ice-water and extracted with dichloromethane, and the solvent was removed from the organic phase. The residue was purified twice by means of column chromatography with the eluent 4:1 dichloromethane:methanol+1% triethylamine. Protected target product was obtained, which was stirred with 1:1 THF:water and 1 g of KOH at 65° C. overnight. After cooling, the reaction mixture was added to water and 15 mL of conc. HCl were added. The mixture was stirred at room temperature for 1 h. Then the mixture was extracted with dichloromethane and the solvent was then removed from the organic phase. The crude product was purified by means of column chromatography with the eluent 4:1 dichloromethane:methanol+2% triethylamine. This gave 610 mg of a red solid, which corresponds to a yield of 54%.

Analytical Data:

$^1$H NMR (500 MHz, DMSO, 25° C.): δ=8.78 (d, 1H); 8.60 (d, 1H); 8.53 (d, 1H); 7.97 (m, 2H); 7.53 (m, 4H); 7.41 (d, 1H); 7.34 (d, 1H); 7.03 (d, 4H); 6.92 (d, 4H); 6.77 (d, 2H); 4.72 (s, 2H); 3.93 (t, 4H); 1.70 (m, 4H); 1.41 (m, 4H); 1.31 (m, 8H); 0.88 (t, 6 h)

Example 5

Compound Occurred as a Mixture of the Isomers 5a and 5b

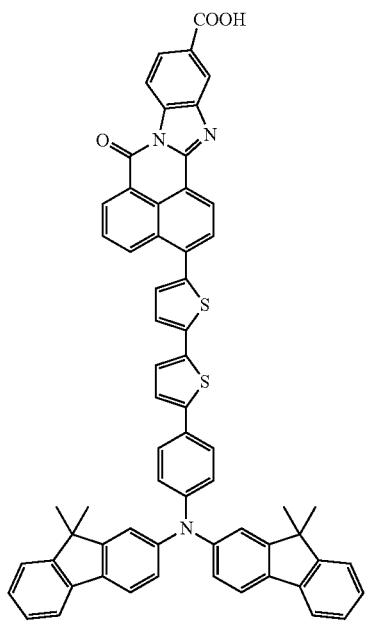

(5a)

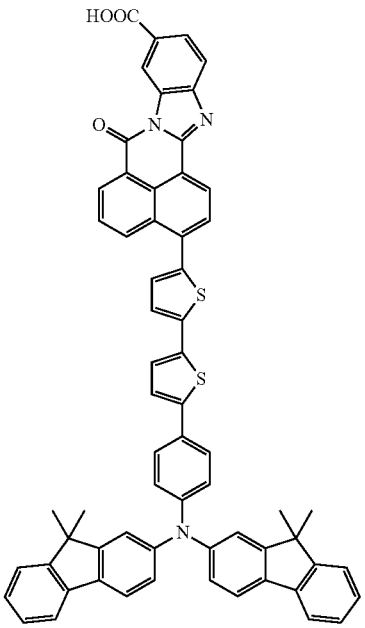

(5b)

[4-(5'-Bromo-[2,2']bisthiophenyl-5-yl)phenyl]bis(9,9-dimethyl-9H-fluoren-2-yl)amine (450 mg, 0.62 mmol) was dissolved in dioxane (15 ml), 5 molar NaOH (0.4 mL, 1.9 mmol) was added and the mixture was degassed with argon for 30 min. Then Pd[P(tBu)$_3$]$_2$ (10 mg, 0.02 mmol) and 6-(4,4,5,5-tetramethyl-[1,3,2]dioxaborolan-2-yl)benzo[de]isochromene-1,3-dione (330 mg, 1 mmol) were introduced and the mixture was stirred at 85° C. overnight. After cooling, the mixture was added to ice-water and extracted with dichloromethane, and the organic phase was concentrated. This gave 490 mg of an orange solid.

Maldi-MS: M+=837.27

6-(5'-{4-[Bis-(9,9-dimethyl-9H-fluoren-2-yl)amino]phenyl[2,2']bithiophenyl-5-yl)-benzo[de]isochromene-1,3-dione (400 mg, 0.48 mmol), zinc acetate (88 mg, 0.22 mmol) and 3,4-diaminobenzoic acid (220 mg, 1.44 mmol) were introduced into quinoline (40 ml). The mixture was heated to 220° C. and stirred for 7 h. After cooling, precipitation was effected with 6% HCl, and the solid was filtered off with suction and washed with hot water and a little ethanol. Column chromatography with 5:1 dichloromethane:methanol gave 98 mg (21%) of an orange solid.

Maldi-MS: M+=953.24

Use Examples

The substrates used were glass plates which had been coated with fluorine-doped tin oxide (FTO) and had dimensions of 25 mm×15 mm×3 mm (Nippon Sheet Glass), which had been treated successively with glass cleaner (RBS 35), demineralized water and acetone, in each case for 5 min in an ultrasound bath, then boiled in isopropanol for 10 minutes and dried in a nitrogen stream.

To produce the solid TiO$_2$ barrier layer, a spray pyrolysis process as described in Peng et al., Coord. Chem. Rev. 248 (2004), 1479, was used. The TiO$_2$ paste DSL 18NR-T (Dyesol) was printed onto the solid TiO$_2$ barrier layer in a screen-printing process. The paste consisted of TiO$_2$ particles with a diameter of approx. 25 nm, which were dispersed in a terpineol/ethylcellulose mixture. After the printing process, the paste was dried at 80° C. for 5 minutes. This was followed by sintering at 450° C. for 30 minutes. The resulting nanoporous TiO$_2$ layer had a layer thickness of 1.8 µm.

For electrical insulation between metal back electrodes and working electrodes, as well as the TiO$_2$ layer, strips of polyimide (Pyrrolin Polyimide Coating, Supelco) were placed along each longitudinal side and cured in a drying cabinet at 200° C. for 15 min.

After removal from the drying cabinet, the sample was cooled to 80° C., immersed into a 5×10$^{-4}$ molar ethanolic solution of hydroxamic acid salt (the salt was obtained by reacting the commercially available hydroxamic acid with sodium hydroxide solution)

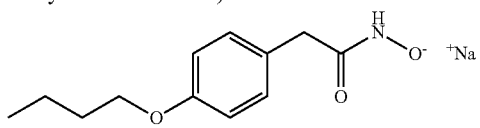

for 16 h, then removed, washed briefly with EtOH and then placed into a 5×10$^{-4}$ molar solution of the inventive dye or a solution of the comparative compound JK2 in dichloromethane for 1 h.

The sample removed from the solution was subsequently rinsed with pure solvent (here dichloromethane) and dried in a nitrogen stream.

A p-conductor solution was spun onto the dried sample. The solution consisted of: 0.16 M spiro-MeOTAD (Merck) in chlorobenzene and 0.3 M LiN(SO$_2$CF$_3$)$_2$ (Aldrich) in cyclohexanone in a ratio of 15:1 and 2.5 percent by weight of V$_2$O$_5$ based on spiro-MeOTAD. 125 µl of this solution were applied to the sample and allowed to act for 60 s. Thereafter, the excess solution was spun off at 2000 rpm for 30 s.

The metal back electrode was applied by thermal metal vaporization under reduced pressure.

For this purpose, the sample was provided with a mask, in order to apply 8 separate back electrodes with dimensions of 0.13 cm$^2$ to the active region. For this purpose, Ag was vaporized at a rate 3.0-3.5 nm/s at a pressure of approx. 5*10$^{-5}$ mbar, so as to result in a layer thickness of 200 nm.

The quantum efficiency (IPCE=Incident Photon-to-current Conversion Efficiency) was measured with a 75 watt xenon arc lamp (LOT-Oriel), a ⅛ m monochromator (SpectraPro-2150i; Acton Research Corporation), a transimpedance amplifier (Aescusoft GmbH Automation) and a lock-in amplifier 7265 (Signal Recovery).

Current/voltage characteristics were obtained at an illumination intensity of 100 mW/cm$^2$ (xenon lamp (LOT-Oriel) with AM1.5 filter) by varying the voltage between −0.6 V and +1.0 V and measuring the resulting short circuit current. The data for different inventive compounds and the prior art compound JK2 are shown in Table 1 (I$_{SC}$: short circuit current, V$_{OC}$: open circuit voltage; FF: fill factor; ETA: efficiency).

TABLE I

| Dye | I$_{sc}$ [mA/cm$^2$] | V$_{oc}$ [mV] | FF [%] | ETA [%] |
|---|---|---|---|---|
| 2a | −7.8 | 820 | 63 | 3.9 |
| 4a | −7.5 | 840 | 61 | 3.8 |
| 3a | −7.4 | 840 | 59 | 3.6 |
| 3a (toluene)* | −7.7 | 860 | 64 | 4.1 |
| 5a/b | −7.8 | 900 | 42 | 2.9 |
| JK2 | −9.2 | 860 | 58 | 4.6 |

*"3a (toluene)" means that the dye was not applied as usual from dichloromethane solution, but from toluene solution.

Figure 1:
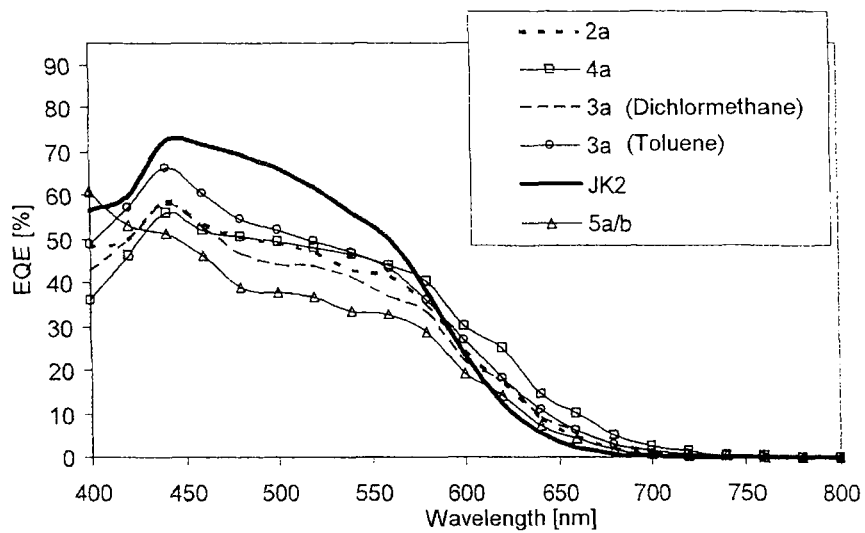
FIG. 1 shows the EQE values of the inventive compounds and of the prior art compound JK2 as a function of wavelength.
Figure 2:
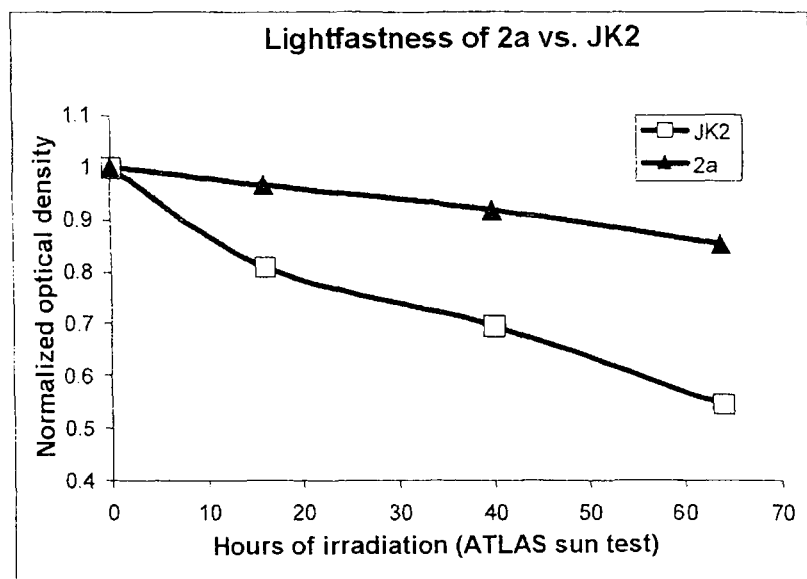
FIG. 2 shows a comparison of the lightfastness of the inventive dye of compound 2a compared to the prior art dye JK2, in each case on TiO$_2$. The irradiation series was commenced after 2 h of "light soaking" in the sun tester.
Figure 3:
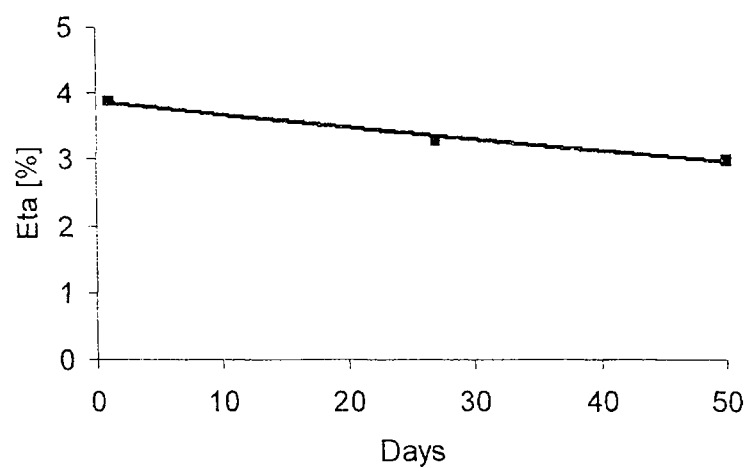
FIG. 3 shows the efficiency of a short-circuited solar cell with dye 2a as a function of time. To determine the efficiency, the current/voltage characteristic was recorded in a Source Meter Model 2400 (Keithley Instruments Inc.) with irradiation using a power of 100 mW/cm$^2$ (xenon lamp (LOT-Oriel) with AM1.5 filter).

The invention claimed is:
1. A compound of the formula Ia or Ib

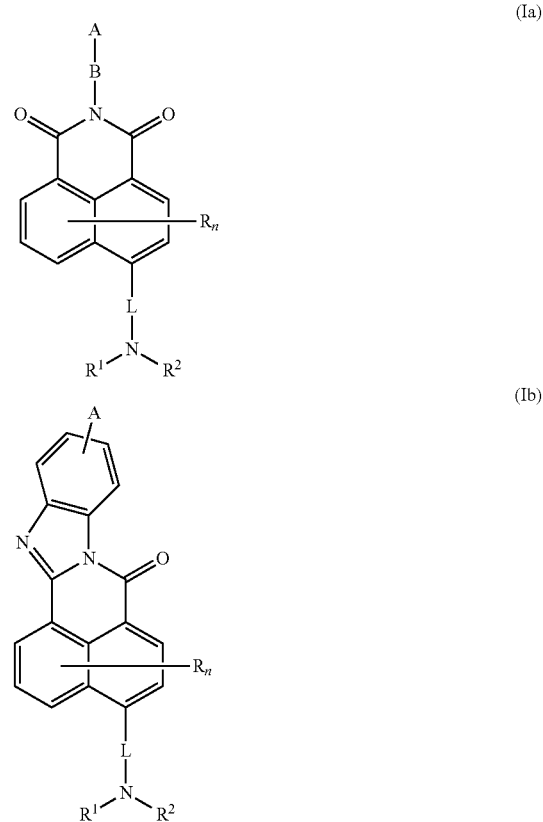

in which
R are identical or different aryloxy, arylthio, hetaryloxy or hetarylthio radicals,
n is 0, 1, 2, 3, 4 or 5,
B is C$_1$-C$_6$-alkylene or 1,4-phenylene, where the phenylene radical may be mono- or polysubstituted by alkyl, nitro, cyano and/or halogen,
A is —COOM, —SO$_3$M or —PO$_3$M,
M is hydrogen, an alkali metal cation or [NR']$_4^+$,
R' is hydrogen or alkyl, where the R' radicals may be the same or different,
L is a bridge of the formula —Ar—, —Ar—Ar— or —Ar—Ar—Ar— which may be mono- or polysubstituted by phenyl, alkyl, alkoxy, alkylthio and/or —NR⁴R⁵, and in which Ar is aryl or hetaryl which may be fused to saturated or unsaturated 5- to 18-membered rings which may comprise heteroatoms which may be the same or different in the case of two or three Ar, R⁴, R⁵ are each independently hydrogen, alkyl whose carbon chain may be interrupted by one or more —O—, —S—, —CO—, —SO— and/or —SO₂— moieties, aryl or hetaryl, each of which may be mono- or polysubstituted by alkyl, alkoxy and/or alkylthio, R¹, R² are each independently radicals of the formula IIa or IIb

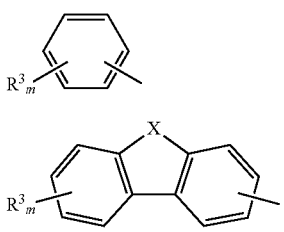

(IIa)

(IIb)

R³ is phenyl, alkyl, alkoxy, alkylthio or —NR⁷R⁸,
m is 0, 1, 2, 3 or 4,
X is C(R⁶R⁷)₂, NR⁸, oxygen or sulfur and
R⁶, R⁷, R⁸ are each independently hydrogen, alkyl whose carbon chain may be interrupted by one or more —O—, —S—, —CO—, —SO— and/or —SO₂— moieties, aryl or hetaryl, each of which may be mono- or polysubstituted by alkyl, alkoxy and/or alkylthio.

2. A compound according to claim 1, wherein, in the formulae Ia and Ib,
R are identical or different aryloxy or arylthio radicals,
n is 0, 1 or 2,
B is C₁-C₆-alkylene,
A is —COOM,
M is hydrogen or an alkali metal cation,
L is a bridge of the formula

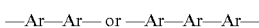

which may be mono- or polysubstituted by phenyl, C₁-C₁₂-alkyl, C₁-C₁₂-alkoxy, C₁-C₁₂-alkylthio and/or —NR⁴R⁵, and in which Ar is identical or different aryl or hetaryl which may be fused to saturated or unsaturated 5- to 18-membered rings which may comprise heteroatoms, R⁴, R⁵ are each independently hydrogen, C₁-C₁₂-alkyl whose carbon chain may be interrupted by one or more —O—, —S—, —CO—, —SO— and/or —SO₂— moieties, R¹, R² are each independently radicals of the formulae II'a and II'b

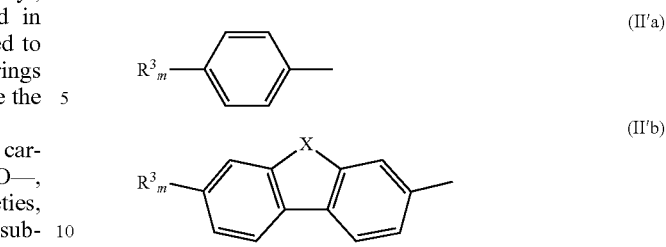

(II'a)

(II'b)

R³ is C₁-C₁₂-alkoxy,
m is 0 or 1,
X is C(R⁶R⁷)₂, NR⁸, oxygen or sulfur and
R⁶, R⁷, R⁸ are each independently hydrogen, C₁-C₁₂-alkyl whose carbon chain may be interrupted by one or more —O—, —S—, —CO—, —SO— and/or —SO₂— moieties.

3. A compound according to claim 1, wherein, in the formulae Ia and Ib,
n is 0,
B is C₁-C₆-alkylene,
A is —COOM,
M is hydrogen or an alkali metal cation,
L is a bridge of the formula

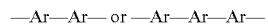

in which Ar is identical or different aryl or hetaryl,
R¹, R² are each independently radicals of the formulae II'a and II'b

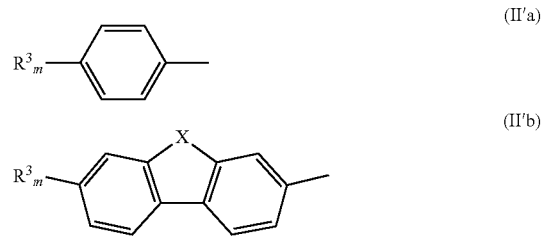

(II'a)

(II'b)

R³ is C₁-C₁₂-alkoxy,
m is 0 or 1,
X is C(R⁶R⁷)₂ and
R⁶, R⁷ are each independently hydrogen or C₁-C₁₂-alkyl.

4. A solar cell or photodetector comprising compounds of the formula Ia or Ib or mixtures of compounds of the formulae Ia and Ib according to any one of claim 1, 2 or 3 and/or isomers or mixtures of the isomers of the compounds of the formulae Ia and Ib according to any one of claim 1, 2 or 3 as photosensitizers.

* * * * *